US010151736B2

(12) United States Patent
Luwang et al.

(10) Patent No.: US 10,151,736 B2
(45) Date of Patent: Dec. 11, 2018

(54) PROCESS FOR THE DETECTION AND ADSORPTION OF ARSENIC

(71) Applicant: COUNCIL OF SCIENTIFIC & INDUSTRIAL RESEARCH, New Delhi (IN)

(72) Inventors: Meitram Niraj Luwang, Pune (IN); Debasish Ghosh, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/503,577

(22) PCT Filed: Aug. 11, 2015

(86) PCT No.: PCT/IN2015/050087
§ 371 (c)(1),
(2) Date: Feb. 13, 2017

(87) PCT Pub. No.: WO2016/024290
PCT Pub. Date: Feb. 18, 2016

(65) Prior Publication Data
US 2017/0241970 A1 Aug. 24, 2017

(30) Foreign Application Priority Data

Aug. 12, 2014 (IN) .......................... 2297/DEL/2014

(51) Int. Cl.
G01N 33/18 (2006.01)
B01J 20/02 (2006.01)
C02F 1/28 (2006.01)
C02F 1/58 (2006.01)
B01J 20/28 (2006.01)
G01N 21/64 (2006.01)
G01N 21/73 (2006.01)
G01N 33/00 (2006.01)
C02F 101/10 (2006.01)
C02F 103/06 (2006.01)

(52) U.S. Cl.
CPC ...... G01N 33/1813 (2013.01); B01J 20/0207 (2013.01); B01J 20/0259 (2013.01); B01J 20/0292 (2013.01); B01J 20/28007 (2013.01); C02F 1/281 (2013.01); C02F 1/58 (2013.01); G01N 21/643 (2013.01); G01N 21/73 (2013.01); C02F 2101/103 (2013.01); C02F 2103/06 (2013.01); C02F 2305/08 (2013.01)

(58) Field of Classification Search
CPC .... G01N 33/1813; G01N 33/18; G01N 33/00; B01J 20/0259; B01J 20/0203; B01J 20/02; B01J 20/00
USPC ................................................. 436/172, 164
See application file for complete search history.

(56) References Cited

U.S. PATENT DOCUMENTS

| 6,197,201 | B1 | 3/2001 | Misra et al. | |
|---|---|---|---|---|
| 7,338,603 | B1 | 3/2008 | McNew et al. | |
| 7,815,854 | B2* | 10/2010 | Cohen | G01N 21/01 422/423 |
| 2004/0050795 | A1 | 3/2004 | Park et al. | |
| 2004/0106207 | A1* | 6/2004 | Lyon | C02F 1/70 436/81 |
| 2006/0207945 | A1 | 9/2006 | Witham et al. | |
| 2011/0220577 | A1 | 9/2011 | Singh et al. | |
| 2014/0001125 | A1 | 1/2014 | El-Safty et al. | |

FOREIGN PATENT DOCUMENTS

WO 2006/115486 A1 11/2006
WO 2012/040650 A2 3/2012

OTHER PUBLICATIONS

Chen et al, Sensitization of Eu3+ Luminescence in Eu:YPO4 Nanocrystals, The Journal of Physical Chemistry C, 2013, 117, 5956-5962. (Year: 2013).*
Lai, Hua et al, UV Luminescence Property of YPO4:RE (RE = Ce3+. Tb3+), J. Phys. Chem. C, 2008, 112, 282-286. (Year: 2008).*
Nedelec, J.M., et al, Soft Chemistry Routes to YPO4-Based Phosphors: Dependence of Textural and Optical Properties on Synthesis Pathways, Chem. Mater., 2002, 14, 651-655. (Year: 2002).*
Feng et al, Adsorption and desorption characteristics of arsenic onto ceria nanoparticles, Nanoscale Research Letters 2012, 7:84, p. 1-8. (Year: 2012).*
Pan et al, Synthesis and red luminescence of Pr3+ - doped CaTiO3 nano-phosphor from polymer precursor, Journal of Solid State Chemistry, 174, 2003, 69-73. (Year: 2003).*
Basu T, et al. Nano-structured iron(III)-cerium(IV) mixed oxide: Synthesis, characterization and arsenic sorption kinetics in the presence of co-existing ions aiming to apply for high arsenic groundwater treat. Applied Surface Science. Oct. 15, 2013; 283:471-481.
Chen HQ, et al. Ultrasensitive mercury(II) ion detection by europium(III)-doped cadmium sulfide composite nanoparticles. Talanta. Nov. 15, 2010;83(1):139-44.
Haider A, et al. Detection of trace amount of arsenic in groundwater by laser-induced breakdown spectroscopy and adsorption. Optics & Laser Technology. Mar. 2014; 56:299-303.
International Search Report for PCT/IN2015/050087, dated Jun. 6, 2016.
Li R, et al. Exceptional arsenic adsorption performance of hydrous cerium oxide nanoparticles: Part A. Adsorption capacity and mechanism. Chem Eng J. Mar. 15, 2012; 185-186:127-135.
Wassay SA, et al. Removal of arsenite and arsenate ions from aqueous solution by basic yttrium carbonate. Water Research. May 1996; 30(5):1143-1148.

(Continued)

Primary Examiner — Christine T Mui
(74) Attorney, Agent, or Firm — McCarter & English, LLP

(57) ABSTRACT

The present invention relates to a process for the detection and adsorption of arsenic from ground water and industrial waste water using lanthanide doped nanoparticles. More particularly, the present invention provides a process for the detection and adsorption arsenic in ppm level using $Eu_{0.05}Y_{0.95}PO_4$ nanoparticles.

4 Claims, 9 Drawing Sheets

(56) References Cited

OTHER PUBLICATIONS

Written Opinion of the International Searching Authority for PCT/IN2015/050087, dated Jun. 6, 2016.
Zhang Y, et al. Arsenic(V) removal with a Ce(IV)-doped iron oxide adsorbent. Chemosphere. Jun. 2003;51(9):945-52.
Lee, Sang-Ho, et al., "Enhanced Arsenate Removal Performance in Aqueous Solution by Yttrium-Based Adsorbents", International Journal of Environmental Research and Public Health, 2015, vol. 12, pp. 13523-13541.

* cited by examiner

PROCESS FOR THE DETECTION AND ADSORPTION OF ARSENIC

CROSS-RELATED APPLICATIONS

This application is a national stage application filed under 35 U.S.C. 371 of PCT/IN2015/050087, filed on Aug. 11, 2015, which claims the benefit of IN Application No. 2297/DEL/2014, filed Aug. 12, 2014, all of which are incorporated by reference herein, in their entirety.

FIELD OF THE INVENTION

The present invention relates to a process for the detection and adsorption of arsenic. More particularly, the present invention relates to a novel process for detection and adsorption of arsenic using lanthanide doped nanoparticles.

BACKGROUND AND PRIOR ART

Arsenic is a well-known carcinogen, and arsenic contamination of groundwater is a widespread occurrence affecting vast regions in India, Bangladesh, China, Mexico, Argentina, and the United States. According to World Health Organization (WHO), permissible limit of conc. of arsenic in water is 10 microgram per liter. Permissible limit of arsenic in industrial waste is 10 ppm. In ground water arsenic remains in two water soluble oxidation states, arsenic (III) and arsenic (V) among which Arsenic(III) is more toxic due to its soft nature. Higher conc. of arsenic in regular drinking water may cause several damages like hyperkeratosis, depigmentation, skin cancer, cancer in the lungs, bladder, liver, kidney and prostate. So detection and removal of arsenic from drinking water is very important for human health. Laboratory techniques used to detect arsenic are atomic fluorescence spectroscopy (AFS), graphite furnace atomic absorption (GFAA), inductively coupled plasma emission spectrophotometry (ICP-AES), inductively coupled plasma mass spectroscopy (ICP-MS), hydride generation atomic adsorption (HGAA), atomic absorption spectrometry (AAS) and neutron activation analysis. Although these methods can accurately measure arsenic in an environmental sample to microgram arsenic per liter concentrations, they require tedious sample preparation and pre concentration procedures, expensive instruments, and professional personnel. Moreover, they cannot be used as portable devices for on-site detection.

Article titled "Detection of trace amount of arsenic in groundwater by laser-induced breakdown spectroscopy and adsorption" by A Haider et al. published in Optics & Laser Technology, March 2014, 56, Pages 299-303 reports LIBS technique coupled with adsorption for the efficient detection of arsenic in liquid. Several adsorbents like tea leaves, bamboo slice, charcoal and zinc oxide have been used to enable sensitive detection of arsenic presence in water using LIBS. Arsenic in water at 1 ppm level reported by a combination of LIBS and adsorption by ZnO.

Article titled "Ultrasensitive mercury(II) ion detection by europium(III)-doped cadmium sulfide composite nanoparticles" by H Q Chen et al. published in Talanta, 2010, 83 (1), pp 139-144 reports Eu3+-doped cadmium sulfide composite nanoparticles synthesized through a straightforward one-pot process. The article also reports a process for the detection of trace $Hg^{2+}$ in aqueous solutions.

US patent application no. 20110220577 discloses a process for the removal of arsenic and Cr(III&VI) from contaminated water using zinc peroxide nanoparticles which comprises treating the contaminated water containing arsenic and chromium with the nanoparticles of zinc peroxide in a ratio (w/v) ranging from 8:1 to 12:1 (mg/ml), having the concentration of arsenic, Cr(III&VI) contamination below 50 ppm in water, at ambient temperature, for a period of 5-10 min, followed by filtration to obtain the desired low concentrated contamination permissible drinking water.

US patent application no. 20060207945 discloses a method for removing arsenic from an aqueous feed which comprises contacting said aqueous feed with solids consisting essentially of a compound containing cerium in the +4 oxidation state to oxidize and remove said arsenic from said feed and thereby produce an aqueous fluid having a reduced arsenic concentration as compared to said aqueous feed, wherein said solids consist essentially of cerium dioxide.

U.S. Pat. No. 6,197,201 discloses a process for removing or stabilizing arsenic and/or selenium from aqueous streams or slurries is provided that includes contacting the streams or slurry with a composition containing lanthanum chloride. The lanthanum chloride composition can optionally contain various lanthanides. These lanthanide series of elements includes the elements lanthanum, cerium, praseodymium, neodymium, promethium, samarium, europium, gadolinium, terbium, dysprosium, holmium, erbium, thulium, ytterbium and lutetium.

PCT application no. 2012040650 discloses a method for treating water and/or a water handling system with one or more rare earths to decrease deposit formation and/or to remove a deposit, wherein the deposit material can comprise one or more of fluoride, arsenite, arsenate, antimonite, bismuthate, pnictogon and the term "Rare earth" refers to one or more of yttrium, scandium, lanthanum, cerium, praseodymium, neodymium, samarium, europium, gadolinium, terbium, dysprosium, holmium erbium, thulium, ytterbium, and lutetium.

Article titled "Removal of arsenite and arsenate ions from aqueous solution by basic yttrium carbonate" by S A Wasay et al. published in Water Research, 1996, 30 (5), pp 1143-1148 reports a new method to remove arsenite and arsenate ions from aquatic systems by using basic yttrium carbonate (BYC). The removal by adsorption of arsenite and arsenate ions was reported to be >99% depending on initial concentration in the pH range of 9.8-10.5 and 7.5-9.0, respectively.

U.S. Pat. No. 7,338,603 discloses a process for removing oxyanions of an element using a sorbent comprising one or more rare earth compounds to remove one or more of said oxyanions, wherein the rare earth compounds are selected from lanthanum, cerium, praseodymium, neodymium, samarium, europium, gadolinium, terbium, dysprosium, holmium, erbium, thulium, ytterbium, lutetium, yttrium and scandium.

Therefore, a new highly effective, reliable, and economical technique is needed to meet the new lowered arsenic maximum contaminant level. The prior cited references indicated about the detection of Arsenic in water in the range of 1-50 ppm level by a combination of LIBS and adsorption by ZnO, Zinc peroxide, Cerium dioxide, lanthanide chloride, yttrium carbonate, etc. Compared to other known and reported techniques, the present invention of arsenic removal systems using adsorption usually do not take up a large amount of space or require additional chemicals for treatment of the water, and do not generate sludge that must be disposed of.

OBJECTIVE OF INVENTION

The main objective of the present invention is to provide a simple and rapid method for the detection and adsorption of arsenic.

Another objective of the present invention is to provide a rapid method for detection of arsenic that may be applicable on field or at the spot of contamination.

SUMMARY OF THE INVENTION

Accordingly, the present invention provides a novel process for detection and adsorption of arsenic using lanthanide doped nanoparticles.

In a preferred aspect, the present invention provides arsenic detection in ppm level using $Eu_{0.05}Y_{0.95}PO_4$ nanoparticles.

DETAILED DESCRIPTION OF THE INVENTION

Figure 1:
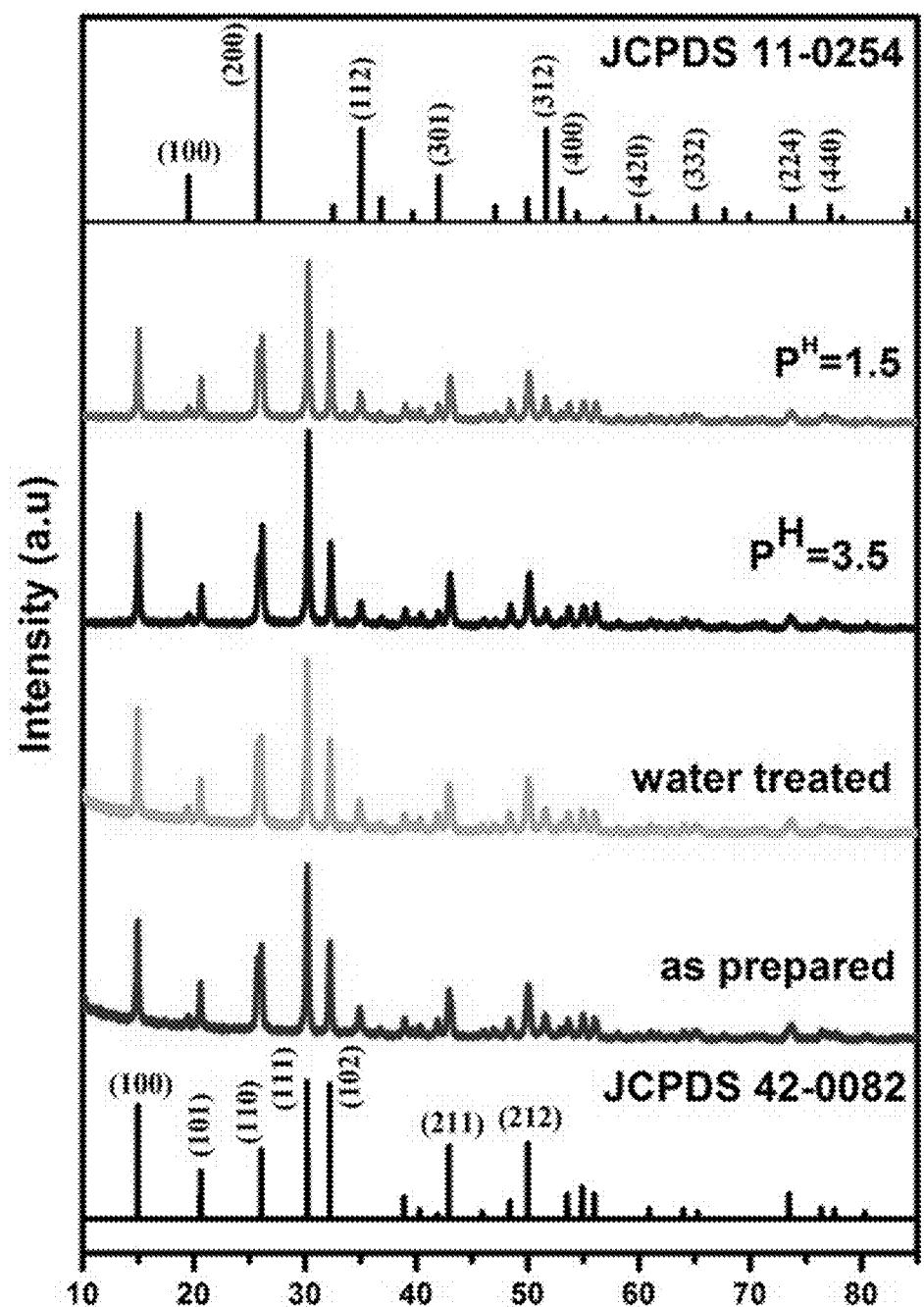
FIG. 1: XRD patterns of $Eu^{3+}$:$YPO_4$ (as prepared, water treated, arsenic adsorbed at pH=1.5 and 3.5) along with JCPDS No. 42-0082 and 11-0254.

The invention will now be described in detail in connection with certain preferred and optional embodiments, so that various aspects thereof may be more fully understood and appreciated.

As used herein, "adsorption" refers to the adherence of atoms, ions, molecules, polyatomic ions, or other substances of a gas or liquid to the surface of another substance, called the adsorbent. The attractive force for adsorption can be, for example, ionic forces such as covalent, or electrostatic forces, such as van der Waals and/or London's forces.

Accordingly, the inventors disclose arsenic detection in ppm level using $Eu_{0.05}Y_{0.95}PO_4$ nanoparticles.

In view of above, the present invention provides a process for flourimetric or Raman spectroscopy detection of Arsenic in water comprising lanthanide doped nanoparticles is disclosed herein, wherein the limit of detection of Arsenic is 10 ppm.

In an embodiment, the present invention provides a process for flourimetric or Raman spectroscopy detection of arsenic in water comprising:
a. Adding lanthanide doped nanomaterials to arsenic solution with >9 ppm at a pH in the range of 1 to 6;
b. Analyzing the arsenic adsorbed on nanoparticles of the solution of step (a) to obtain photoluminescence effect.

In preferred embodiment, the lanthanide doped nanoparticle comprises europium and ytterbium.

In another preferred embodiment, the lanthanide doped nanoparticle is $Eu_{0.05}Y_{0.95}PO_4$.

In another preferred embodiment, the size of lanthanide doped nanoparticle is 1-2 μm in length and 20 nm in width.

The arsenic containing water is selected from hard or soft ground water, effluent, domestic or potable water.

The process of the present invention can detects arsenic at a concentration greater than 9 ppm.

In one embodiment, the present invention provides $Eu^{3+}$ (5%) doped hexagonal $YPO_4$ nanoparticles prepared by co-precipitation method and are used for arsenic detection.

In another preferred embodiment the present invention provides $Eu^{3+}$ (5%) doped hexagonal $YPO_4$ nanoparticles which are stable in acidic medium.

Adsorption of arsenic on the surface of lanthanide doped nanoparticles reduces the luminescence intensity of the doped lanthanide ions. This change in luminescence property may be used to detect arsenic in ground water and the lanthanide doped nanomaterials are also a good adsorbent. In the emission spectra of $Eu^{3+}$, intensity ratio of magnetic transition (591 nm) and the electrical transition (617 nm) is influenced by the environment around the lanthanide ion.

In yet another preferred embodiment, the invention provides a process of detection of Arsenic wherein the process detects arsenic at a concentration greater than 9 ppm.

In another aspect, the present invention provides using the luminescence enhancement and quenching properties of the nanoparticles for the detection of both arsenic and arsenous acid in the industrial waste.

In still another aspect, the lanthanide doped $Eu_{0.05}Y_{0.95}PO_4$ nanoparticles may be synthesized by methods known in the art.

In an embodiment of the invention, the present invention provides a process, which detects arsenic at a concentration greater than 9 ppm, producing visual change in luminescence.

In a preferred embodiment, the nanoparticles are synthesized by co-precipitation method.

Amount of arsenic adsorbed by the nanoparticles are measured by inductively coupled plasma atomic emission spectroscopy (ICP-AES). (Table 2)

The following examples, which include preferred embodiments, will serve to illustrate the practice of this invention, it being understood that the particulars shown are by way of example and for purpose of illustrative discussion of preferred embodiments of the invention.

EXAMPLES

Reagents and Materials:

Yttrium(III) nitrate hexahydrate, $Y(NO_3)_3$, $6H_2O$ (99.9%), ammonium dihydrogen phosphate, $(NH_4)H_2PO_4$ (99.999%), polyethylene glycol (PEG) from Sigma-Aldrich. Arsenic(III) oxide, $As_2O_3$ sodium hydroxide, hydrochloric acid, Glycerol from Merck was used without further purification. Deionized water was used throughout the experiment.

Example 1: Synthesis of $YPO_4$:$Eu^{3+}$ Nanorods $Eu_{0.05}Y_{0.95}PO_4$ nanoparticles were synthesised by co-precipitation method. Stoichoimetric amounts of $Y(NO_3)_3.6H_2O$ (1.582 g), $Eu(NO_3)_3.5H_2O$ (0.093 g), and 3 g of PEG were dissolved in a mixture of 40 ml of water and 60 ml of ethylene glycol (EG). The mixture was stirred at 80° C. for half an hour. Then a solution of 0.5 g of $(NH_4)H_2PO_4$ in 10 ml of deionised water was added slowly to the reaction mixture and refluxed at 140° C. for three hour in a 250 ml round bottom flask fitted with a condenser under water circulation. The resulting white precipitate was collected by centrifuging at 10,000 rpm after washing with water and methanol. The precipitate was dried in an oven at 100° C. temperature and used as sensing material for arsenic. (FIG. 1)

Example 2

Figure 2:
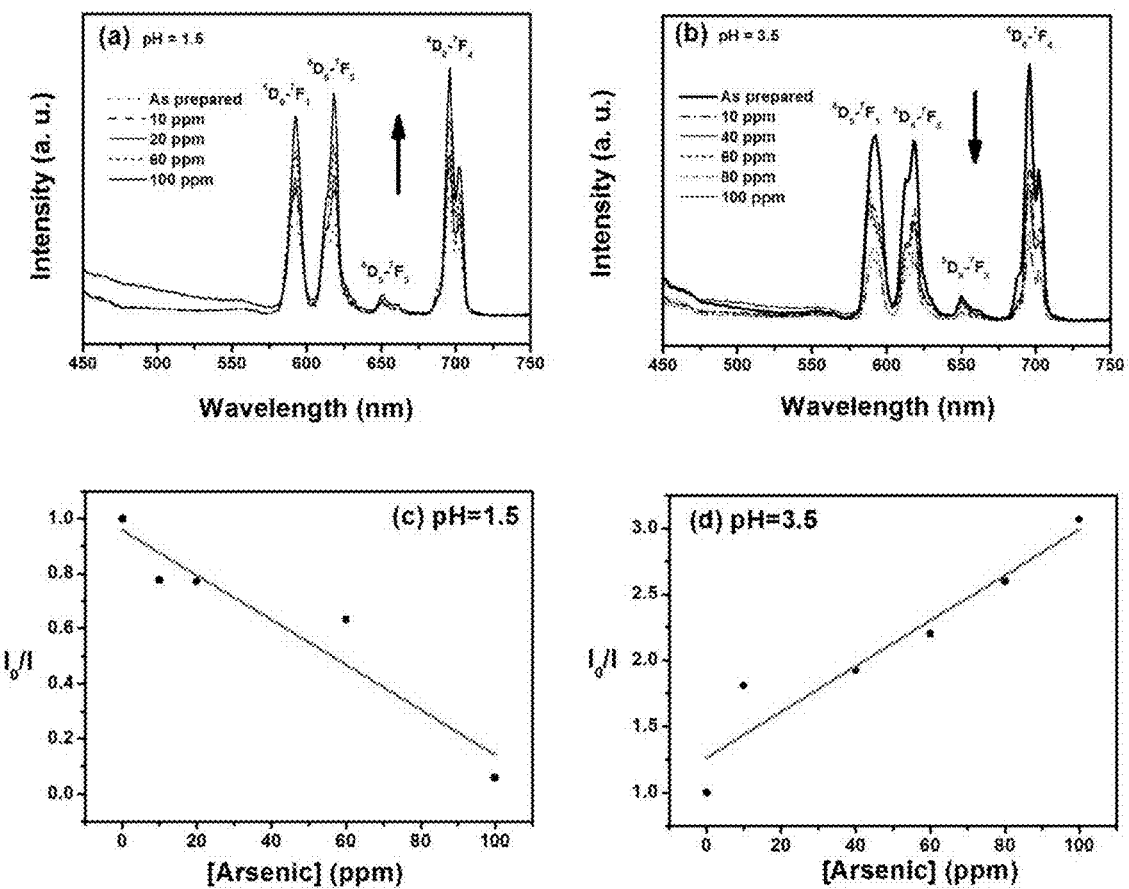
FIG. 2: PL spectra of arsenic $YPO_4$:$Eu^{3+}$ after arsenic adsorption at pH=1.5 and 3.5 along with variation of asymmetric ratio.
Figure 3:
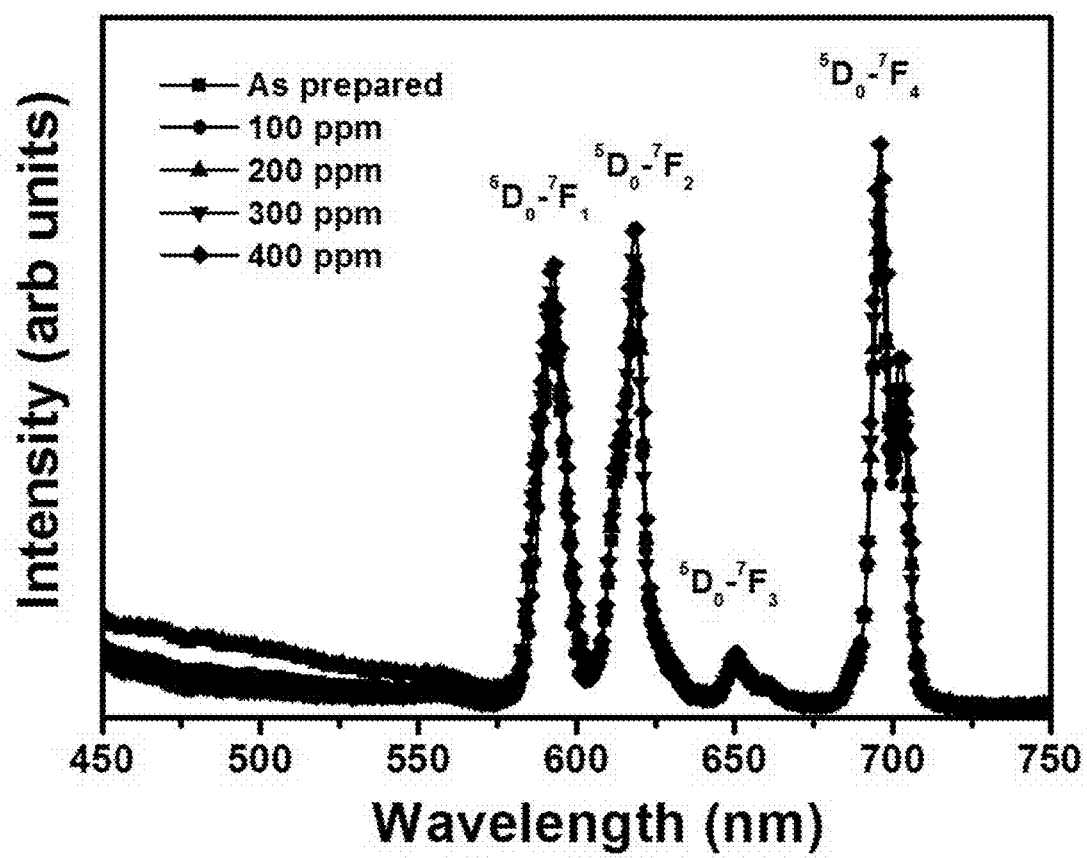
FIG. 3: PL spectra of Chlorine effect.
Figure 4:
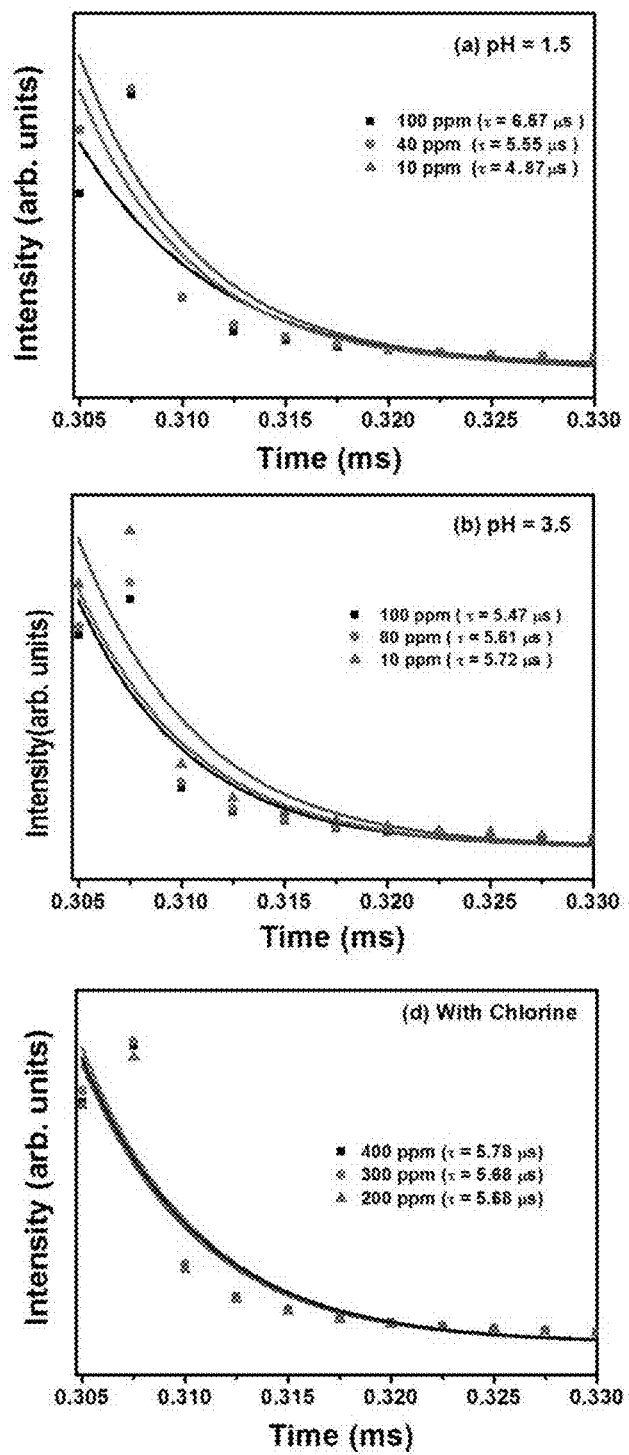
FIG. 4: Life time measurements of arsenic and chloride adsorbed samples.
Figure 5:
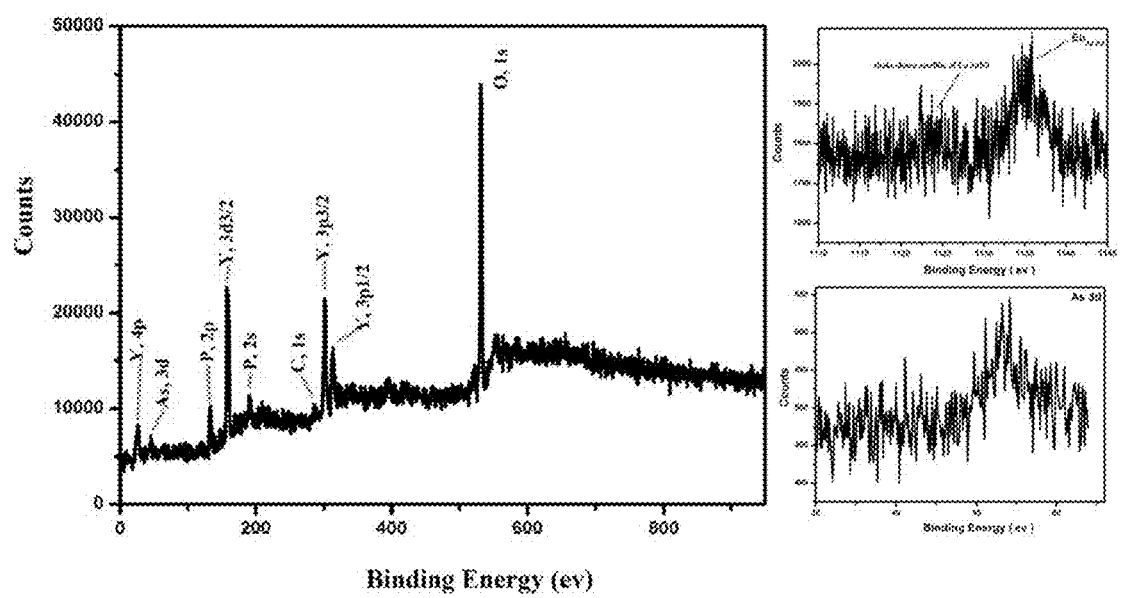
FIG. 5: XPS spectra of the arsenic adsorbed sample.
Figure 6:
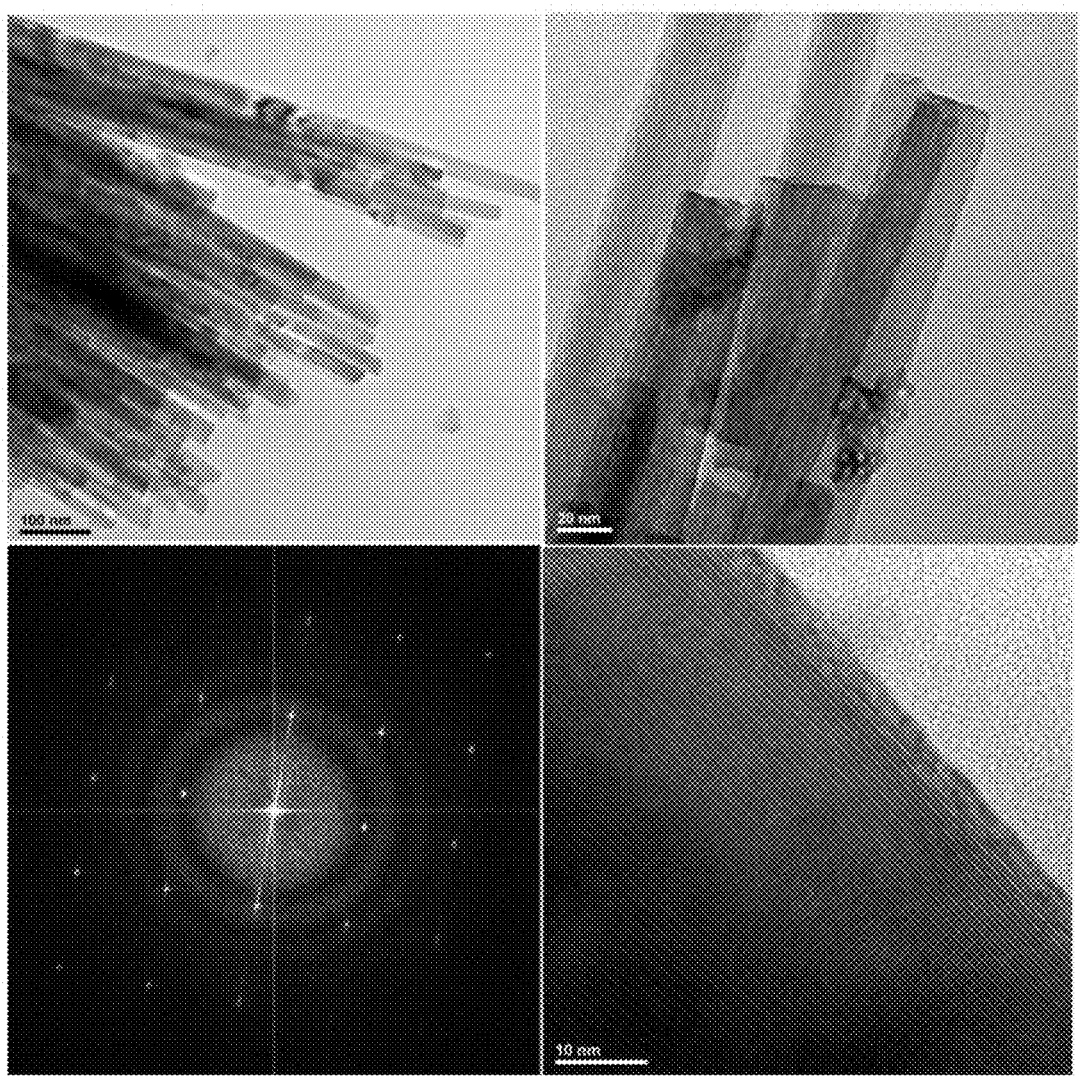
FIG. 6: TEM images of $Eu^{3+}$:$YPO_4$ nanomaterials treated with As solution, SAED pattern and the lattice fringe.
Figure 7:
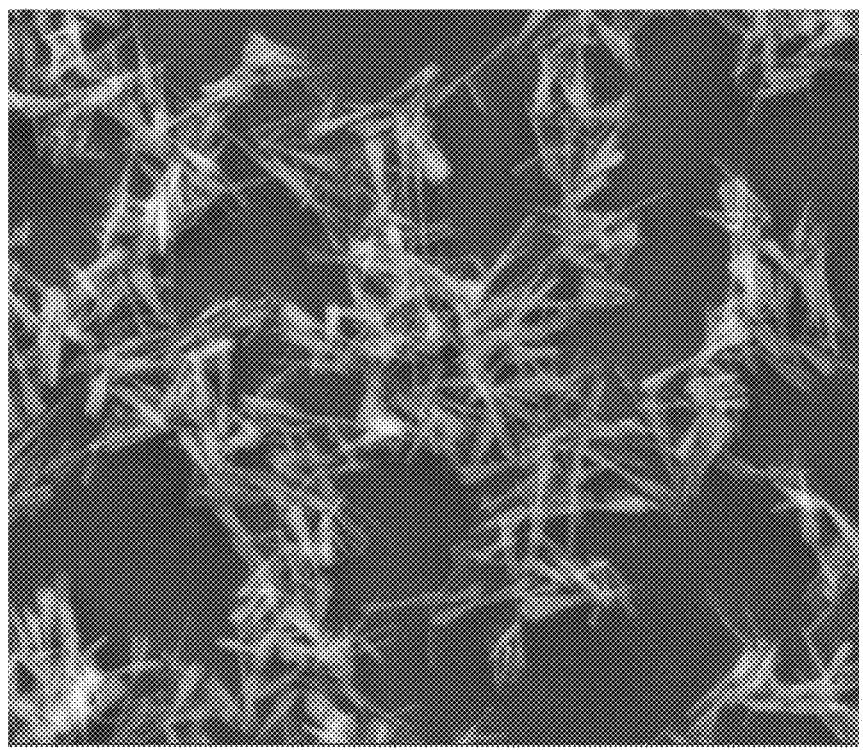
FIG. 7: SEM images and EDAX spectra of arsenic adsorbed $Eu^{3+}$:$YPO_4$ nanoparticles.
Figure 7:
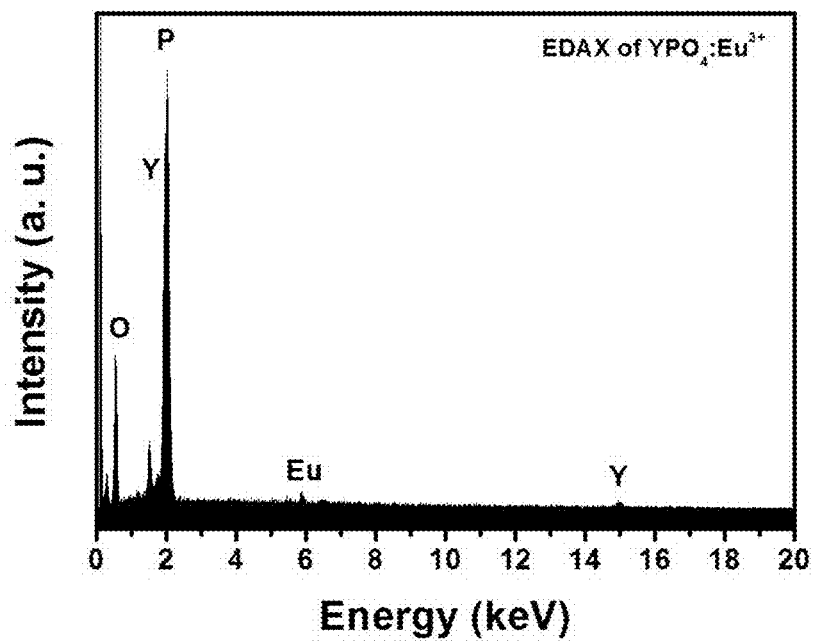
Figure 8:
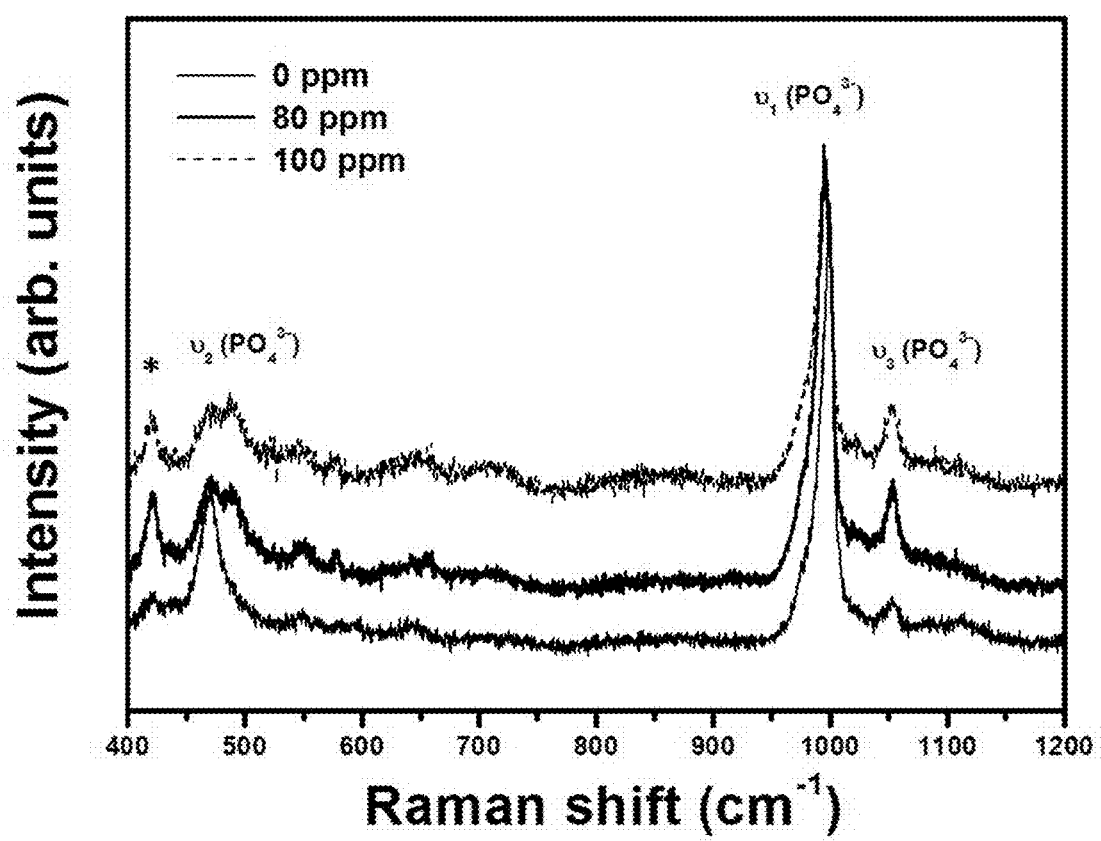
FIG. 8: Raman spectra of $Eu^{3+}$:$YPO_4$ at different concentrations of As solution (a) 0, (b) 80 and (c) 100 ppm.
Figure 9:
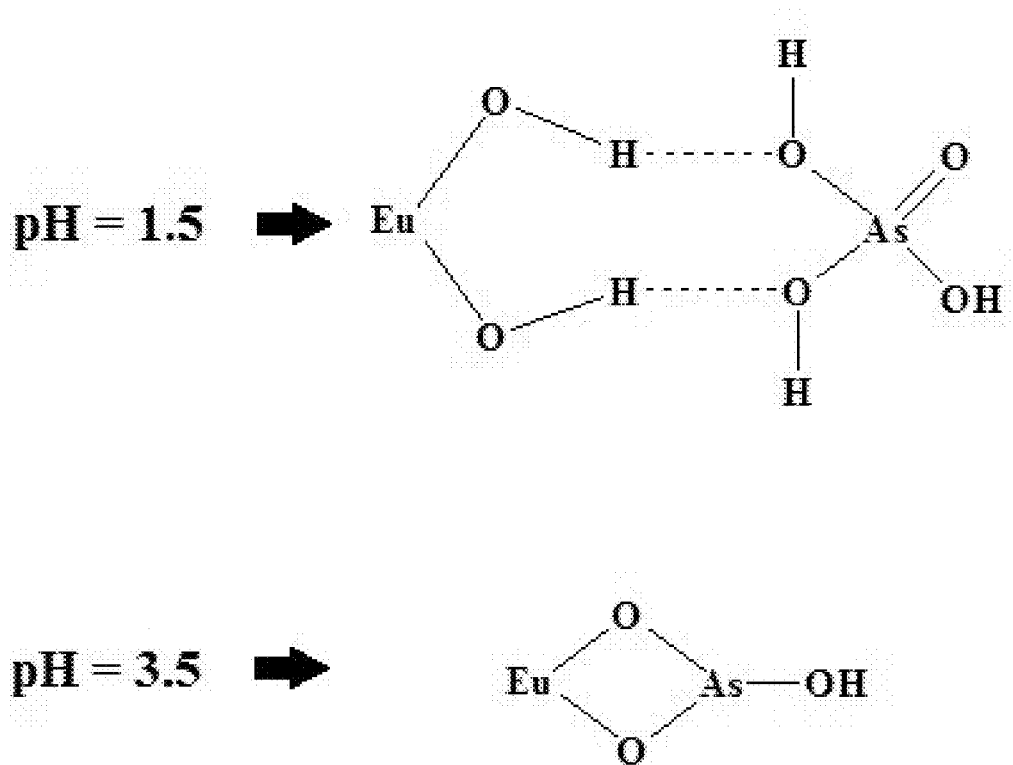
FIG. 9: Schematic diagram for the interaction of As ion with the nanomaterials.

Preparation of 100 ppm Arsenic (III) Solution: (FIG. 2, 3)
At pH=1.5

132 mg of $As_2O_3$ was dissolved in 10 ml 1(N) NaOH solution. 2 ml conc. HCl was added and diluted with deionised water to 100 ml. This solution was further diluted with 2% (V/V) HCl solution to 1000 ml to get an arsenic solution of 100 ppm strength. pH of this arsenic solution is 1.5.

At pH=3.5

132 mg of $As_2O_3$ was dissolved in 10 ml 1(N) NaOH solution. 1 ml conc. HCl was added and diluted with deionised water to 100 ml. This solution was further diluted with 1% (V/V) HCl solution to 1000 ml to get an arsenic solution of 100 ppm strength. pH of this arsenic solution is 3.5. These standard arsenic solutions were further diluted with 2% and 1% of HCl solutions respectively to get solutions of different concentrations. Only freshly prepared arsenic solutions were used for surface adsorption reactions to prevent arial oxidation of arsenic.

Example 3: Adsorption of Arsenic on $YPO_4$:$Eu^{3+}$ Surface

To each 50 ml solution of arsenic of different conc. (100 ppm, 80 ppm, 60 ppm, 40 ppm, 20 ppm, 10 ppm), 0.15 g of $Eu_{0.05}Y_{0.95}PO_4$ nanoparticles were added and stirred at room temperature for three hours. Then the arsenic adsorbed nanoparticles were collected by centrifuging at 10000 rpm and washing with methanol. These collected nanoparticles were dried at 150° C. temperature and their corresponding analyses were performed. (FIG. 4-9)

Example 4: Photoluminescence Study

Photoluminescence study of pure nanoparticles and arsenic adsorbed nanoparticles were performed. On excitation at 375 nm and 395 nm $Eu^{3+}$ showed its characteristic red light emission. The experimental study indicates that on arsenic adsorption, luminescence intensity is much reduced. This decrease in luminescence intensity due to adsorption (surface complex formation and non-radiative thermal quenching) may be used to detect arsenic conc. in ground water. (Table 1)

At pH=1.5 the electronic predominates over magnetic transition with increase in the arsenic concentration which we observed in the increasing asymmetric ratio ($I_{AS}$). At pH=3.5 electronic transition and magnetic transitions are almost equal or magnetic transition predominating.

To determine the amount of arsenic adsorbed by the nanoparticles inductively coupled plasma mass spectroscopy was performed with mother and the filtrate arsenic solutions. The ICP-AES analysis shows that some definite quantity of the arsenic species is adsorbed by the nanoparticles. Amount of adsorption is higher at higher concentration of arsenic and it is low at lower concentration. This analysis support the interaction of arsenic with the nanoparticles and the enhancement trend observed in the luminescence spectra. (Table 2)

TABLE 1

Relation between arsenic concentration and asymmetric ratio (I).

| | | Area of peak | | |
| --- | --- | --- | --- | --- |
| Sl. No. | Arsenic Concentration (ppm) | Electric transitions ($^5D_0 \rightarrow {}^7F_2$) ($A_e$) | Magnetic transitions ($^5D_0 \rightarrow {}^7F_1$) ($A_m$) | Asymmetric ratio ($I = A_e/A_m$) |
| 1 | pH = 1.5    0 | 112374.21938 | 119382.59727 | 0.94 |
| 2 | 10 | 143034.95019 | 143748.94145 | 0.99 |
| 3 | 20 | 144614.91105 | 141406.28489 | 1.02 |
| 4 | 60 | 178697.97057 | 173600.00968 | 1.03 |
| 5 | 100 | 191237.05734 | 165359.29374 | 1.15 |
| 6 | pH = 3.5    0 | 216934.30064 | 229095.76553 | 0.94 |
| 7 | 10 | 119028.93677 | 209459.68526 | 0.56 |
| 8 | 40 | 111569.8393 | 185278.86541 | 0.60 |
| 9 | 60 | 99067.39673 | 174811.64582 | 0.56 |
| 10 | 80 | 83159.20339 | 91497.84235 | 0.90 |
| 11 | 100 | 70293.04284 | 74149.92192 | 0.94 |

TABLE 2

ICP-AES data showing percentage change in As concentration.

| Sl. no. | Mother solution (ppm) | Filtrate solution (ppm) | Change in concentration (ppm) | % change |
| --- | --- | --- | --- | --- |
| 1 | 67.022 | 61.265 | 5.757 | 8.58 |
| 2 | 53.655 | 50.05 | 3.605 | 6.72 |
| 3 | 39.45 | 38.205 | 1.245 | 3.15 |
| 4 | 26.165 | 24.89 | 1.275 | 4.87 |
| 5 | 12.265 | 12.055 | 0.21 | 1.71 |
| 6 | 6.405 | 6.355 | 0.05 | 0.78 |

Results

The photoluminescence study of pure nanoparticles and arsenic adsorbed nanoparticles are performed. On excitation at 375 nm and 395 nm $Eu^{3+}$ showed its characteristic red light emission. The experimental study indicates that on arsenic adsorption, luminescence intensity is much reduced. This decrease in luminescence intensity due to adsorption (surface complex formation and non-radiative thermal quenching) may be used to detect arsenic conc. in ground water. (Table 1) At pH=1.5 the electronic predominates over magnetic transition with increase in the arsenic concentration which is observed in the increasing asymmetric ratio ($I_{AS}$). At pH=3.5 electronic transition and magnetic transitions are almost equal or magnetic transition predominating. To determine the amount of arsenic adsorbed by the nanoparticles inductively coupled plasma mass spectroscopy are performed with mother and the filtrate arsenic solutions. The ICP-AES analysis shows that some definite quantity of the arsenic species is adsorbed by the nanoparticles. Amount of adsorption is higher at higher concentration of arsenic and it is low at lower concentration. This analysis support the interaction of arsenic with the nanoparticles and the enhancement trend observed in the luminescence spectra. (Table 2).

ADVANTAGES OF INVENTION

Detects very low concentration of As

Avoids expensive analytical instruments

Portable kits may be made, making detection on site easy

Works for analyte that may be hard or soft ground water, effluent, domestic or potable.

We claim:

1. A process for the detection of arsenic in water comprising the steps of:
   a) adding lanthanide doped nanoparticles to an arsenic solution at a pH in the range of 1 to 6;
   b) adsorbing arsenic from the arsenic solution by the lanthanide doped nanoparticles; and
   c) observing a photoluminescence effect to analyze the arsenic adsorbed on the lanthanide doped nanoparticles;
   wherein said lanthanide doped nanoparticle is $Eu_{0.05}Y_{0.95}PO_4$, and wherein a limit of detection of arsenic is 10 ppm.

2. The process as claimed in claim 1, wherein the lanthanide doped nanoparticles are each 1-2 μm in length and about 20 nm in width.

3. The process as claimed in claim 1, wherein arsenic containing water is selected from hard or soft ground water, effluent, domestic or potable water.

4. The process as claimed in claim 1, wherein said process detects arsenic, producing a visual change in luminescence.

* * * * *